Figure 1:
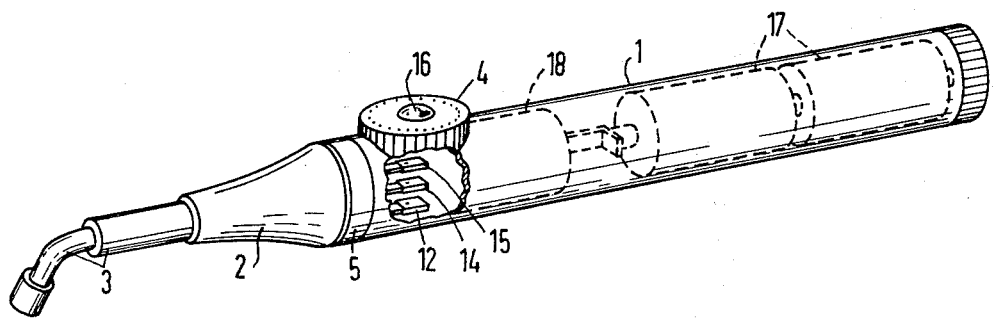

United States Patent [19]
Landgraf

[11] 3,943,919

[45] Mar. 16, 1976

[54] ELECTRICAL TOOTH PULP TESTER HAVING TILTABLE HEAD

[75] Inventor: Hermann Landgraf, Bensheim, Germany

[73] Assignee: Siemens Aktiengesellschaft, Munich, Germany

[22] Filed: Mar. 13, 1972

[21] Appl. No.: 233,672

[52] U.S. Cl. ............................ 128/2.1 R; 324/72.5
[51] Int. Cl.$^2$ .................. A61B 19/00; G01R 31/02
[58] Field of Search ............... 324/72.5; 128/2.1 R; 200/61.58, 61.85, 61.55, 61.56

[56] References Cited
UNITED STATES PATENTS

| | | | |
|---|---|---|---|
| 1,548,184 | 8/1925 | Cameron | 128/2.1 R |
| 1,738,755 | 12/1929 | Blackmore | 200/61.55 |
| 1,768,513 | 6/1930 | Denyes | 200/61.55 |
| 2,119,752 | 6/1938 | Pulleybank | 200/61.55 |
| 2,515,004 | 7/1950 | Haupt | 324/72.5 |
| 2,522,052 | 9/1950 | Logan | 128/2.1 R |
| 2,595,623 | 5/1952 | Yonkers | 324/72.5 |

*Primary Examiner*—Alfred E. Smith
*Attorney, Agent, or Firm*—Richards & Geier

[57] ABSTRACT

An apparatus for connecting a testing electrode to a source of electrical energy having a housing for receiving a testing electrode and a member for connecting the testing electrode to a source of electrical energy. The invention is particularly characterized by contact means disposed about a common line, which face each other, and which are spaced apart by spring means, the arrangement being such that contact between the contact means of said housing and the contact means of said member can be effected by relative displacement of said housing and said member in the direction of said common line or by relative tilting of said housing and said member in any direction.

7 Claims, 3 Drawing Figures

U.S. Patent   March 16, 1976   3,943,919

ELECTRICAL TOOTH PULP TESTER HAVING TILTABLE HEAD

This invention relates to apparatus for connecting a testing electrode to a source of electrical energy. The invention is especially applicable to electric pulp testers which comprise, as a source of energy, a battery housed in a handpiece, with a testing head mounted on the handpiece for receiving an active electrode.

Electric pulp testers should be easy to manipulate, and this means that it must also be possible for the instrument to be operated with a minimum number of manipulations. Known constructions comprise, in addition to an operating member for setting up the exciting current, a separate manually operable on-off switch. It may very readily happen that, on completion of the testing operation, it is forgotten to switch off the pulp testing instrument. The result of this is that electric component parts remain live after the testing time. In the case of battery-operated instruments, current is unnecessarily consumed and the battery can all too readily become rapidly discharged. This is of particular importance in the case of "cordless" pulp testers in which the battery is housed in the handpiece of the pulp testing instrument.

According to the invention there is provided apparatus for connecting a testing electrode to a source of electrical energy, including a housing for receiving a testing electrode, and a member for connection to a source of electrical energy, wherein said housing and said member are each provided with contact means disposed about a common line, which face each other and which are spaced apart by spring means, the arrangement being such that contact between the contact means of said housing and the contact means of said member can be effected by relative displacement of said housing and said member in the direction of said common line or by relative tilting of said housing and said member in any direction.

Figure 2:
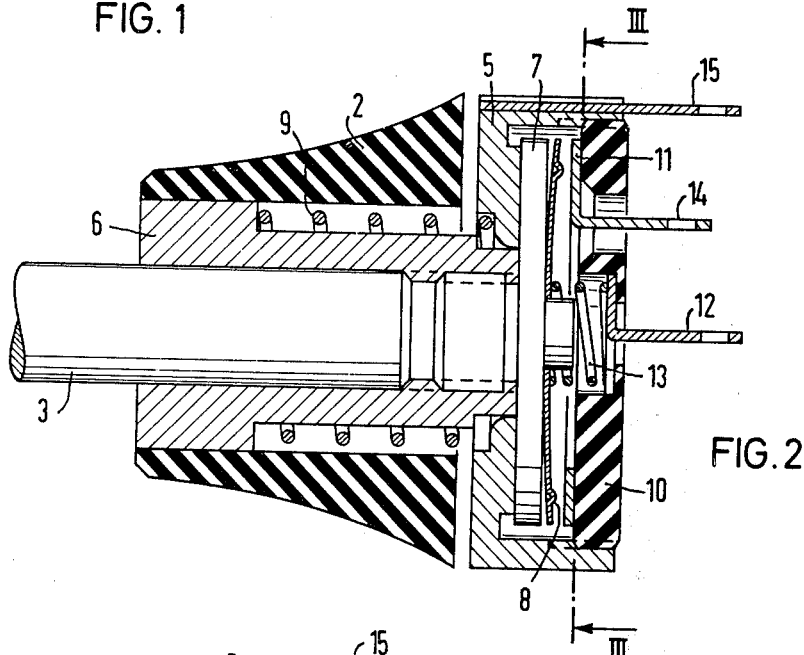
Figure 3:
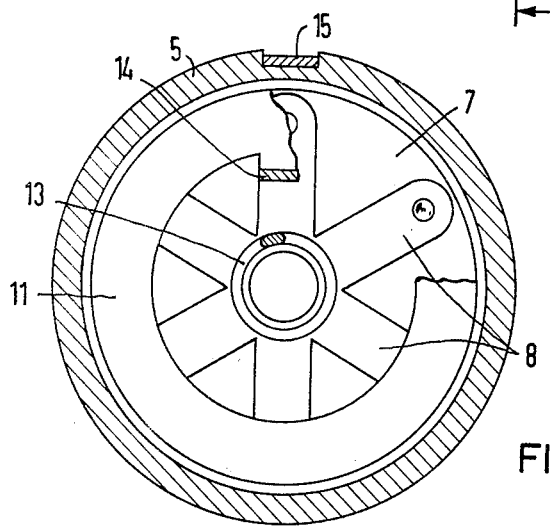

In order that the invention may be fully understood and readily carried into effect it will now be described with reference to the accompanying drawing, in which:

FIG. 1 is a perspective view of an electric pulp tester in accordance with the invention, FIG. 2 is a longitudinal section through part of the apparatus of FIG. 1, and FIG. 3 is a part cut-away transverse section on the line III — III of FIG. 2.

FIG. 1 illustrates an electric pulp testing instrument comprising a rod-shaped handpiece 1 and a testing head 2. There are housed in the handpiece 1 batteries 17 and a block 18 including the electric component elements necessary for the generation of the exciting current. The testing head 2 receives an active electrode 3, the bent-over end of the testing tip of which is applied against the tooth to be tested. For adjusting the necessary intensity of the exciting current, there is provided an actuating element 4 which is provided with graduations, from which the intensity of the exciting current can be read. Attached to the handpiece is a housing 5, against which the testing head 2 bears with the interposition of spring elements. The housing 5 receives switching elements for switching the instrument on and off. The spring elements so space the testing head 2 away from the handpiece 1 and the housing 5 that it can readily be tilted in any direction and also shifted in the direction of the axis of the handpiece.

Details of the mounting and of the arrangement of the switching elements in the housing 5 are shown in FIGS. 2 and 3.

The testing head 2 includes an inner sleeve 6, in which the active electrode 3 is disposed. The sleeve 6 is connected at its innermost end to an insulating disc 7 on which there are disposed a number of contact tongues 8, preferably six. The parts 2, 6, 7 and 8 are spaced away from the switch housing 5, which is secured to the handpiece 1, by means of a compression spring 9. The switch housing 5 is substantially pot-shaped and is screwed on to a receiving member 10 associated with the handpiece 1. The receiving member 10 consists of insulating material and has a contactring 11 on the side opposite the contact tongues 8. The contact tongues 8 are arranged on the insulating disc 7 so as to extend radially away from its central axis, and are electrically connected together. The connection to the contact tongues 8 is effected by means of a contact lug 12 and a spring 13. The contact lug 12 is connected to the battery, and a connecting member 14 extending out of the contact ring 11 is connected to the input of the electronic system for the generation of the exciting current. The output of the electronic system is connected to a connecting portion 15, which is in turn conductively connected to the switch housing 5. The contact between the active electrode 3 and the switch housing 5 is made by way of the compression spring 9. The active electrode 3 may be pushed or screwed into the sleeve 6.

The handpiece 1 includes also a lamp 16 for indicating contact between the contact means 12 and 14.

When the testing tip is pressed on to the tooth to be tested, at least one of these six contact tongues 8 comes into contact with the contact ring 11, whereby the circuit extending from the battery through the connecting lug 12 to the input of the electronic system is closed. When the testing tip, and hence the testing head 2, is relieved of load, the spring 9 lifts the contact tongues 8 from the contact ring 11, whereby the circuit is broken. On contactmaking, there may initially be energised an indicator, for example a pilot lamp, which serves to indicate to the surgeon when the pulp testing instrument is ready for operation.

The compression spring 9 is preferably so dimensioned that the switching contacts between the contact tongues 8 and the contact ring 11 are closed substantially at a bearing pressure in the range from 10 to 100 pond (i.e. 10 to 100 g.dynes)

What we claim is:

1. Electrical pulp tester, comprising a handpiece, a testing head extending from one end of the handpiece and having a probe, adapted to be applied to a patient's tooth for testing its pulp, spring means connecting said handpiece with said testing head for a tiltable movement relatively to said handpiece and for a shiftable movement axially to the handpiece, a source of power within said handpiece for providing current supplied to the probe, switching means connecting said source of power with said probe for supplying and interrupting the supply of the current to said probe, said switching means having contact members arranged upon said testing head and other contact members arranged on said handpiece and adapted to close when said testing head is tilted or shifted.

2. Pulp tester according to claim 1, wherein the contact members upon said testing head comprise a plurality of radially extending contact tongues and the contact members upon said handpiece comprise a ring shaped contact member.

3. Pulp tester according to claim 2, wherein said switching means comprise a switch housing, said contact members being located within said housing, and a spring connected with said housing and urging the contact members away from each other.

4. Pulp tester according to claim 3, comprising means connecting said switch housing to the handpiece.

5. Pulp tester according to claim 4, wherein the last-mentioned means detachably connect said switch housing to the handpiece.

6. Pulp tester according to claim 1, wherein said source of power consists of a battery.

7. Pulp tester according to claim 1, comprising means indicating a contact between the first-mentioned contact members and said other contact members.

* * * * *